United States Patent [19]

Mansour et al.

[11] Patent Number: 4,508,821

[45] Date of Patent: Apr. 2, 1985

[54] DETECTION OF WHITE CELL ASSOCIATED BACTERIA WITH A FLUORESCENT DYE

[75] Inventors: James D. Mansour, Raleigh; Thomas Schulte, Cary, both of N.C.

[73] Assignee: Becton Dickinson and Company, Paramus, N.J.

[21] Appl. No.: 510,537

[22] Filed: Jul. 5, 1983

[51] Int. Cl.$^3$ .......................... C12Q 1/04; C12Q 1/06
[52] U.S. Cl. .................................. 435/34; 250/461.2; 435/6; 435/39; 436/63; 436/94; 436/172
[58] Field of Search .................. 424/3, 7.1; 435/6, 29, 435/34, 39, 820; 436/63, 94, 172, 175, 177; 250/461.2

[56] References Cited

U.S. PATENT DOCUMENTS

| | | | |
|---|---|---|---|
| 3,700,555 | 10/1972 | Widmark et al. | 435/29 X |
| 3,864,212 | 2/1975 | Berkhan | 436/175 X |
| 4,094,745 | 6/1978 | Scholefield | 435/39 |
| 4,225,783 | 9/1980 | Palin et al. | 436/172 X |
| 4,257,774 | 3/1981 | Richardson et al. | 435/6 X |
| 4,330,410 | 5/1982 | Takenaka et al. | 210/927 X |
| 4,330,622 | 5/1982 | Desai | 435/34 |
| 4,400,370 | 8/1983 | Kass | 424/7.1 X |

OTHER PUBLICATIONS

Kostiala et al., Am. J. Clin. Pathol., vol. 72, pp. 437–443, (1981).
Coppen et al., J. Clin. Pathol., vol. 34, pp. 1375–1377, (1981).
Brooks et al., Arch. Intern. Med., vol. 132, pp. 673–675, (1973).
Reik et al., J. Am. Med. Asso., vol. 245, pp. 357–359, (1981).
Faden, J. Pediatrics, vol. 88, pp. 1032–1034, (1976).
Kronvall et al., Acta. Path. Microb. Scand., vol. 85, pp. 249–254, (1977).
McCarthy et al., J. Clin. Microb., vol. 11, pp. 281–285, (1980).
Goldner et al., Laboratory Med., vol. 14, pp. 291–294, (May 1983).
Roser, Soil Biol. Biochem., vol. 12, pp. 329–336, (1980).
Steen et al., Cytometry, vol. 1, pp. 32–36, (1980).

*Primary Examiner*—Arnold Turk
*Assistant Examiner*—Robert J. Hill, Jr.
*Attorney, Agent, or Firm*—Richard E. Brown

[57] ABSTRACT

A method for detection of intracellular bacteria in a blood sample by staining with ethidium bromide and observing microscopically using fluorescence is provided. The bacteria stain rapidly and selectively and are detectable in complex mixtures. The bacteria may be in whole blood or may optionally be partially isolated or purified before staining.

29 Claims, No Drawings

DETECTION OF WHITE CELL ASSOCIATED BACTERIA WITH A FLUORESCENT DYE

FIELD OF THE INVENTION

This invention relates to the partial separation and detection of bacteria. More particularly, it relates to the detection of bacteria in a sample wherein the bacteria are differentiated from other components of the sample by selective staining with a fluorescent dye.

DESCRIPTION OF THE PRIOR ART

Blood is normally a sterile fluid. However, when contaminating microorganisms are present, the resulting infections are life threatening situations. Even with modern drug treatment, the mortality rate from septicemia (blood poisoning) is approximately 25%, a figure which rises to 60% when shock is also present. For successful treatment of blood infections, early diagnosis is obviously of great importance, since proper treatment cannot be initiated until accurate identification of the pathogen has been accomplished. This is rendered very difficult in the early stages of the infection because the concentration of the pathogen in the blood is very low.

A standard method for concentration of bacteria prior to identification utilizes culturing techniques. In general, this procedure consists of growing bacteria from the sample in a suitable medium to such a concentration as to allow plating onto a solid agar medium with subsequent recovery as a relatively pure concentrated sample. This growth requirement is obviously time consuming and constitutes a severe drawback since rapid identification of the pathogen is of paramount importance.

Culturing can sometimes be avoided if the bacteria are partially separated or purified from some of the other components in the sample which might mask their presence and thereby hinder detection and subsequent identification. Standard methods available in the art for concentrating or isolating bacteria from such samples have relied on specific physical properties of the bacteria, such as size or density. However, use of such techniques is complicated by the fact that different species of bacteria differ greatly in these properties. More recent methods, allowing rapid identification of bacteria are counterimmunoelectrophoersis, latex agglutination and radioimmunologic methods. Such methods, although successful in certain situations, have been much less successful in detection of circulating bacteria, especially during the early stages of infection.

Leukocytes bound to bacteria are known in the art to aid in the isolation of bacteria. Leukocytes (white blood cells) as known in the art, include lymphocytes, monocytes, and granulocytes, and the term "leukocytes" as used herein refers to one or more of these subclasses.

One method which has achieved some limited success in serious blood infections such as septicemia is microscopic examination of smears made from the buffy coat. In this procedure, unclotted blood is centrifuged whereby the buffy coat forms from various blood components including leukocytes, as a thin layer between the plasma and erythrocyte layers. Recent studies (A. Kostialia et al. Am. J. Clin. Pathol. 72, 437 (1981)) have shown that, in rabbits, experimental bacteremias and fungemias induced by innoculations of a variety of pathogens could be detected regularly by microscopy or subculture of the buffy coat when cell populations reached 300–1000/ml. However, in clinical studies (M. J. Coppen, et al. J. Clin. Pathol. 34, 1375 (1981)) it has been shown that the procedure has little practical value because of the high incidence of false positives and negatives.

One of the primary functions of leukocytes is to ingest and destroy microorganisms invading the peripheral blood. The process of ingestion is referred to as phagocytosis, and bacteria thus ingested are hereinafter referred to as intracellular bacteria. Such bacteria are extremely difficult to stain, and in those samples in which phagocytosis has removed all or most of the bacteria, currently available staining techniques, which are capable of staining only free bacteria, are very unreliable.

Clinical microbiology laboratories have often sought to detect bacterial infections by visualizing and scoring leukocytes containing intracellular bacteria. In the present state of the art, intracellular bacteria are visualized under the microscope in blood smears or "buffy coat" smears stained with a variety of standard agents such as Gram, Wright, Jenner-Giemsa, Leishman, or May-Grunwald-Giemsa stains. However, these methods stain not only the bacteria, but also the white cells (nuclei and cytoplasma) and, to a certain extent, other blood components such as platelets and red blood cells. The presence of these other stained bodies makes it difficult not only to locate the bacteria (which are normally present in small numbers) but also to differentiate between the bacteria and other stained white cell components and debris.

Accordingly, there is a need for a better method for the rapid detection of extracellular and intracellular bacteria in body fluid samples. The present invention provides a method which fulfills this need.

The use of fluorescence microscopy for a variety of purposes is increasing in both clinical and research laboratories and has been used in a variety of inexpensive staining protocols. For example, acridine orange has been utilized to selectively stain bacteria in various clinical samples, including blood (L. R. McCarthy and J. E. Senne, J. Clin Microb, 11 281 (1980); G. Kronvall and E. Myhre, Acta Path. Microb. Scand, 85, 249 (1977)). Ethidium bromide has been used extensively to stain both eukaryotic and prokaryotic cells. However, none of these techniques has utilized fluorescence microscopy to detect and differentiate intracellular bacteria in a blood sample.

SUMMARY OF THE INVENTION

Applicants have found that intracellular bacteria can be rapidly and easily detected using fluoresence after staining with ethidium bromide. This staining procedure can be applied to whole blood, buffy coat, or isolated white blood cell fractions such as those obtained from density gradient systems and is effective for the detection of either free or intracellular bacteria.

Thus it is an object of this invention to provide a method for the staining or intracellular bacteria. It is a further object to provide a method for staining bacteria when applied to a leukocyte rich fraction containing both intracellular and free bacteria. It is a further object of this invention to provide a method for allowing easy location of the white blood cells for bacterial scoring by providing a staining method wherein intracellular bacteria stain almost immediately while the white blood cell nuclei stain more slowly. It is a further object of this invention to provide a staining technique of high specificity for intracellular bacteria which eliminates confusion between stained intracellular bacteria and other white cell components. It is a further object of this invention to provide a method for detecting intracellular bacteria which is rapid, inexpensive and does not require sophisticated instrumentation.

DETAILED DESCRIPTION OF THE INVENTION

According to the procedure of this invention, bacteria, either free or intracellular, are stained with ethidium bromide and thereby visualized. Most bacteria stain under the conditions of this invention, as, for example, *S. aureus, E. coli, Strep. fecalis, S. epidermidis, Proteus mirabilis, P. aeruginosa, Bacteroides, fragilis, Klebsiella pneumoniae, H. influenza,* and *N. meningitidis.*

The invention is best demonstrated by adding the bacteria to be stained and thereby detected to a suitable sample fluid. The bacteria can be grown in any suitable medium as for example, trypticase soy broth, and removed during the log growth phase. A quantity of cells, from about $10^4$ to $10^8$, preferably about $10^6$, are washed with saline, suspended in normal saline, and the suspension mixed thoroughly with the sample fluid in a ratio of 1 volume part of cell suspension and from about 5 to about 50 volume parts of sample. Preferably a 10 volume percent suspension is used. Sample fluids which may be used are whole blood or whole blood pretreated with an anticoagulent such as heparin, ethylenediamine tetraacetic acid (hereinafter referred to as EDTA) or with sodium polyanethol sulfonate. Alternatively, purified or partially purified blood components, such as platelet-rich-plasma (hereinafter referred to as PRP), isolated by such techniques known to the practitioner as centrifugation, or leukocyte fractions isolated by such techniques known to tne practitioner as density gradient centrifugation, dextran sedimentation procedures, differential centrifugation, and absorption or entrapment in polymer fibers may be used. The leukocyte fractions thus isolated are suspended in saline before addition of bacteria.

The mixture of cells and fluid is incubated at 37° for from about 10 minutes to about 2 hours, preferably about 30 minutes to allow the leukocytes and bacteria to become associated. Alternatively, the staining may be done without prior incubation. If the bacteria to be detected are in a clinical blood sample suspected of contamination, the whole blood or a PRP sample may be stained directly. Alternatively, a blood fraction, such as the buffy coat or a leukocyte fraction may be isolated by any of the techniques described above and suspended in saline before staining.

After the optional incubation step, staining is carried out in the presence of an aqueous staining buffer comprising sodium borate, EDTA, formaldehyde and a surface active agent such as Triton-X-100. In a preferred embodiment, these components are present in the buffered sample in final concentrations of 40 mM, 24 mM, 0.02% and 0.02% respectively. The buffered bacteria-sample mixture is then treated with a 0.001 percent by weight aqueous solution of ethidium bromide. The amount of dye to be added will be determined by the bacteria and the sample being used, and in general, the final concentration of dye may be varied from about 1 to about 1000 ug per ml of final volume, preferably from about 10 to about 50 ug/ml. The ratio of sample to buffer to dye is preferably 7 parts:2 parts:1 part by volume.

The sample mixture containing the dye is incubated briefly and 0.01 ml is withdrawn and spread over a microscope slide and observed for from about 1 minute to about 1 hour using excitation light at a suitable wavelength below 520 nm., preferably 515 nm., and observing emitted light at wavelengths above 580 nm. The bacteria, whether free or intracellular, stain almost immediately, and staining of the bacteria is complete in 5 minutes or less. Blood components such as platelets and erythrocytes do not stain at all. The nuclei of the leukocytes stain slowly and begin to fluoresce in 10 to 20 minutes. Staining of the leukocytes is complete in about 1 hour. By means of these different staining characteristics, it becomes very easy to differentiate free bacteria, intracellular bacteria and leukocytes. Accurate bacterial scoring is thereby greatly facilitated.

The following examples are provided to further illustrate the invention but are not to be construed in any way as limiting the scope of the invention.

EXAMPLE 1

A. A suspension of about $10^6$ cells of *E. coli* in 10 ul of normal saline was added to 1 ml of EDTA whole blood. This mixture was either stained immediately or preincubated for 30 min. at 37° C. Staining was accomplished by incubating 0.7 ml of the mixture with 0.2 ml of staining buffer (100 mM sodium borate, 60 mM EDTA, 0.05% each of formaldehyde and Triton X-100, ph 9.2.) Forty five ul of this mixture was mixed with 5 ul of a 0.001% solution of ethidium bromide. Immediately after mixing, a microscope slide was prepared and fluorescence observed at wavelengths greater than 580 nm.

B. As in A, except with *S. aureus.*

C. As in A, except *E. coli* was used with heparinized whole blood.

D. As in C, except with *S. aureus.*

E. As in A, except *E. coli* was used with PRP.

F. As in E, except with *S. aureus.*

EXAMPLE 2

This experiment was carried out to determine the effects of incubation temperature and ethidium bromide concentration on staining. Heparinized whole blood was used with *E. coli, S. aureus* and *Strep. fecalis.* The procedure was as described in Example 1. Incubation was carried out for 30 minutes at both room temperature and 37° C. The concentration of ethidium bromide was 10, 25 and 50 ug/ml.

Staining of the bacteria occurred both rapidly and almost completely with both free and intracellular cells and was better in heparinized blood than in EDTA-blood for all 3 species. Staining of the bacteria occurred at different intensities depending on conditions, but was always more intense and more rapid than the leukocytes. Dye concentration was not important except for its effect on the background color (higher dye concentrations gave lighter backgrounds). Temperature of incubation was not important. The time between staining and observation was an important factor. The bacteria stained very rapidly, usually within 1 to 5 minutes. The leukocytes stained more slowly, reaching a yellow-orange in about 1 hour. Platelets and erythrocytes did not stain at all. These results are summarized in TABLE 1.

TABLE 1

% CELLS STAINING WITH ETHIDIUM BROMIDE
AS A FUNCTION OF TIME
BACTERIA ADDED TO HEPARINIZED HUMAN BLOOD

| Time (min) | E. coli | Staph. aureus | Strep. fecalis | Leukocytes | Erythrocytes | Platelets |
|---|---|---|---|---|---|---|
| 1 | 100 | 80 | 100 | <1 | 0 | 0 |
| 5 | 100 | 100 | 100 | 10 | 0 | 0 |
| 10 | 100 | 100 | 100 | 10 | 0 | 0 |
| 30 | 100 | 100 | 100 | 20 | 0 | 0 |

EXAMPLE 3

An example using the method of this invention for isolation and detection of bacteria in a patient having suspected bacteremia is as follows:

Blood is drawn from a patient having suspected bacteremia, and overlaid on a sterile density gradient (composition 57.6% v/v Percoll, 1% Tween 80, made isoosmotic in normal saline) in a volume ratio of 1 part blood to 6 parts gradient. The gradient is then centrifuged for 15 min. at 20,000×G at 5° C. Following centrifugation, a portion of the gradient, corresponding to the location of the blood leukocytes, is removed and suspended in normal saline. Bacteria, if present, are generally located in this fraction. This suspension of leukocytes and possible bacteria is stained with ethidium bromide and examined microscopically as described in Example 1.

What is claimed is:

1. A method for the detection of bacteria including intracellular bacteria comprising staining said bacteria with ethidium bromide, applying excitation light to said bacteria, and observing said bacteria for fluorescence prior to the appearance of fluorescence from any substantial number of leukocyte nuclei.

2. The method in accordance with claim 1 wherein said bacteria are in a blood fraction sample.

3. The method in accordance with claim 2 wherein said blood fraction sample is a platelet-rich-plasma fraction.

4. The method in accordance with claim 2 wherein said blood fraction sample is a leukocyte fraction.

5. The method in accordance with claim 2 wherein said blood fraction sample is the buffy coat.

6. The method in accordance with claim 1 wherein said bacteria are in a whole blood sample.

7. The method in accordance with claim 6 wherein said whole blood sample is treated with an anticoagulant before staining.

8. The method in accordance with claim 7 wherein a blood fraction sample is isolated from said anticoagulated whole blood sample before staining.

9. The method in accordance with claim 7 wherein said anticoagulant is selected from the group consisting of heparin, ethylenediamine tetraacetic acid and sodium polyanethol sulfonate.

10. The method in accordance with claim 9 wherein the anticoagulant is heparin.

11. The method in accordance with claim 9 wherein the anticoagulant is ethylenediamine tetraacetic acid.

12. The method in accordance with claim 9 wherein the anticoagulant is sodium polyanethol sulfonate.

13. A method for the detection of bacteria including intracellular bacteria in whole blood comprising the steps of
    (a) treating said whole blood with an anticoagulant, and a staining mixture comprising a staining buffer and ethidium bromide;
    (b) applying excitation light to said whole blood; and
    (c) detecting any bacteria by observing said whole blood for fluorescence prior to the appearance of fluorescence from any substantial number of leukocyte nuclei.

14. A method in accordance with claim 13 wherein the concentration of said ethidium bromide in the staining mixture is from about 1 to about 100 ug/ml.

15. A method in accordance with claim 13 wherein said whole blood is observed at a wavelength of greater than 580 nm. after excitation below 520 nm.

16. A method in accordance with claim 13 wherein said staining buffer comprises sodium borate, ethylenediamine tetraacetic acid, formaldehyde and Triton-X-100 in water.

17. A method in accordance with claim 16 wherein said staining buffer comprises 100 millimolar sodium borate, 60 millimolar ethylenediamine tetraacetic acid, 0.05% formaldehyde and 0.05% Triton-X-100 in water.

18. A method for the detection of bacteria including intracellular bacteria in whole blood comprising the steps of
    (a) treating said whole blood with an anticoagulant;
    (b) isolating a leukocyte fraction;
    (c) suspending said leukocyte fraction in saline;
    (d) treating said saline suspension with a staining mixture comprising a staining buffer and ethidium bromide;
    (e) applying excitation light to said suspension; and
    (f) detecting any bacteria by observing said suspension for fluorescence prior to the appearance of fluorescence from any substantial number of leukocyte nuclei.

19. A method in accordance with claim 18 wherein the concentration of said ethidium bromide in the staining mixture is from about 1 to about 100 ug/ml.

20. A method in accordance with claim 18 wherein said suspension is observed at a wavelength of greater than 580 nm. after excitation below 520 nm.

21. A method in accordance with claim 18 wherein said staining buffer comprises sodium borate, ethylenediamine tetraacetic acid, formaldehyde and Triton-X-100 in water.

22. A method in accordance with claim 21 wherein said staining buffer comprises 100 millimolar sodium borate, 60 millimolar ethylenediamine tetraacetic acid, 0.05% formaldehye and 0.05% Triton-X-100 in water.

23. A method in accordance with claim 18 wherein said leukocyte fraction is isolated by fractionation on a sterile density gradient.

24. A method in accordance with claim 23 wherein said density gradient is composed of 57.6 volume percent Percoll and 1 volume percent Tween 80 made isoosmotic in normal saline.

25. A method for the detection of bacteria including intracellular bacteria in whole blood comprising the steps of
    (a) treating said whole blood with an anticoagulant;
    (b) isolating the buffy coat fraction;
    (c) suspending said buffy coat fraction in saline;
    (d) treating said saline suspension with a staining mixture comprising a staining buffer and ethidium bromide;
    (e) applying excitation light to said suspension; and
    (f) detecting any bacteria by microscopically observing said suspension for fluorescence prior to the appearance of fluorescence from any substantial number of leukocyte nuclei.

26. A method in accordance with claim 25 wherein the concentration of said ethidium bromide in the staining mixture is from about 1 to about 100 ug/ml.

27. A method in accordance with claim 25 wherein said suspension is observed at a wavelength of greater than 580 nm. after excitation below 520 nm.

28. A method in accordance with claim 25 wherein said staining buffer comprises sodium borate, ethylenediamine-tetraacetic acid, formaldehyde and Triton-X-100 in water.

29. A method in accordance with claim 28 wherein said staining buffer comprises 100 millimolar sodium borate, 60 millimolar ethylenediamine tetraacetic acid, 0.5% formaldehyde and 0.05% Triton-X-100 in water.

* * * * *